US006990903B2

(12) United States Patent
Butland

(10) Patent No.: US 6,990,903 B2
(45) Date of Patent: Jan. 31, 2006

(54) KIT FOR LABELING VALUABLES FOR THEIR IDENTIFICATION AND METHOD THEREFOR

(75) Inventor: Charles L. Butland, Marina del Ray, CA (US)

(73) Assignee: Print-Lock Corporation, Las Vegas, NV (US)

( * ) Notice: Subject to any disclaimer, the term of this patent is extended or adjusted under 35 U.S.C. 154(b) by 0 days.

(21) Appl. No.: 10/829,318

(22) Filed: Apr. 21, 2004

(65) Prior Publication Data

US 2005/0235848 A1    Oct. 27, 2005

(51) Int. Cl.
  *B41K 1/42* (2006.01)
(52) U.S. Cl. ........................ 101/333; 101/108; 101/327
(58) Field of Classification Search ................ 101/103, 101/108, 327, 333, 368; 434/81, 83, 84, 434/85, 88
  See application file for complete search history.

(56) References Cited

U.S. PATENT DOCUMENTS

| | | | |
|---|---|---|---|
| 2,970,539 A * | 2/1961 | Griffin ........................ 101/368 |
| 3,831,518 A * | 8/1974 | Pittman ...................... 101/368 |
| 4,604,062 A * | 8/1986 | Woods ......................... 434/88 |
| 5,228,858 A * | 7/1993 | Fromm ......................... 434/84 |
| 5,448,950 A * | 9/1995 | Lowder et al. ............. 101/333 |
| 5,599,578 A | 2/1997 | Butland |
| 6,030,657 A | 2/2000 | Butland et al. |
| 6,203,069 B1 | 3/2001 | Outwater et al. |
| 6,274,873 B1 | 8/2001 | Outwater et al. |
| 6,354,501 B1 | 3/2002 | Outwater et al. |
| 6,415,714 B2 * | 7/2002 | Winston ..................... 101/327 |
| 6,536,672 B1 | 3/2003 | Outwater et al. |
| 2004/0076460 A1 * | 4/2004 | Yu et al. ........................ 401/1 |

FOREIGN PATENT DOCUMENTS

JP           07 195890 A  *  8/1995

* cited by examiner

*Primary Examiner*—Ren Yan
(74) *Attorney, Agent, or Firm*—Mueller and Smith, LPA

(57) ABSTRACT

Kit for labeling an object for identification thereof includes an inkpad containing an ink bearing an ultra-violet (UV) radiation sensitive dye, a binder, a first biologic mark, and being invisible in the absence of UV light. The kit also includes an integral writing instrument housing a UV light and an ink pen bearing ink that bearings a UV dye and a second biologic marker. The kit further contains an ink pen housing an ink bearing a UV dye and a third biologic marker, and being invisible in the absence of UV light. An inventory list to record objects labeled with said kit is included in the kit additionally.

16 Claims, 2 Drawing Sheets

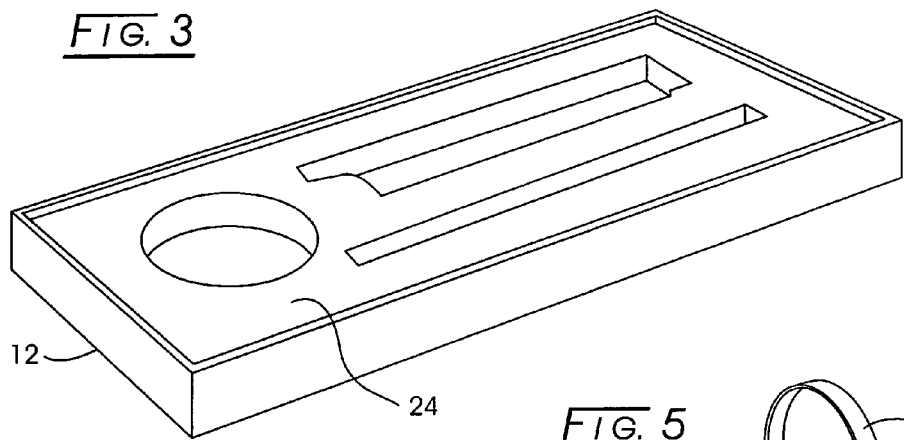
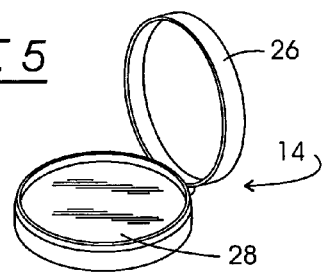
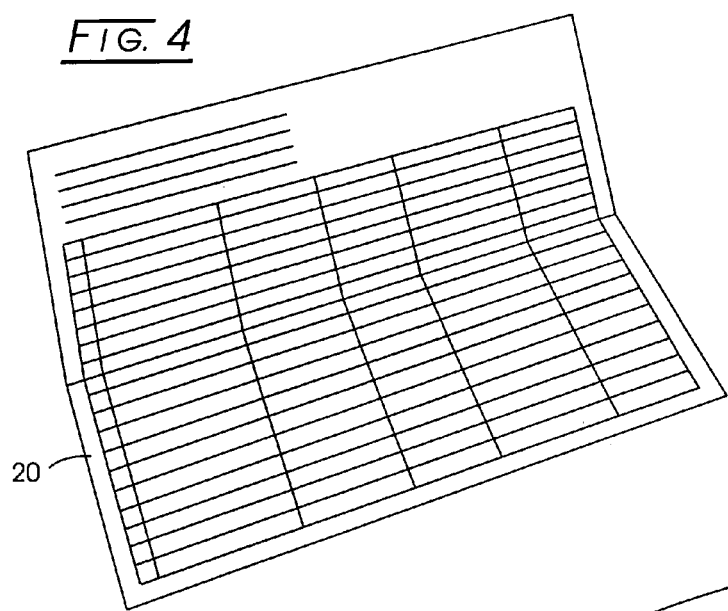
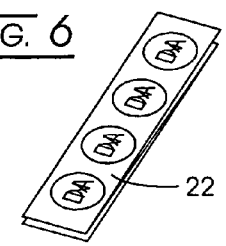
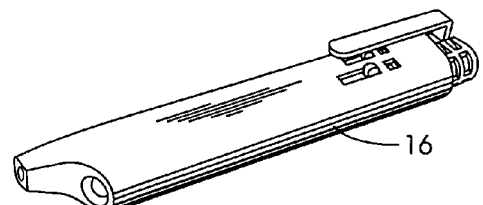
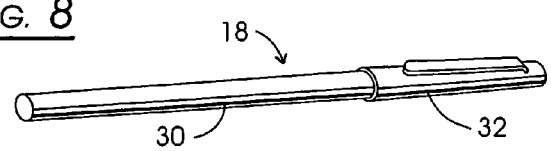

US 6,990,903 B2

KIT FOR LABELING VALUABLES FOR THEIR IDENTIFICATION AND METHOD THEREFOR

CROSS-REFERENCE TO RELATED APPLICATIONS

This application is cross-referenced to Applicant's co-pending application Ser. No. 10/624,296, filed on Jul. 22, 2003.

BACKGROUND OF THE INVENTION

The present invention generally relates to identifying valuables when they are lost or stolen and more particularly to a do-it-yourself kit for labeling valuables and other objects for their identification and for verifying ownership.

Many objects require verification for authentication purposes. Such objects include, inter alia, paintings, sculptures, cartoon cells, sports and other collectibles, and like works of art; videocassette recorders (VCRs), televisions, and like household electronic equipment; and computers, printers, CD players, and like office and business equipment. Other instances of identification in order to verify ownership, include, for example, records, audio and video tape cassettes, computer software recorded on floppy disks/compact discs/diskettes, perfumes, designer clothes, handbags, briefcases, automobile/airplane parts, securities (e.g., stock certificates), wills, identification cards (driver's licenses, passports, visas, green cards), credit cards, smart cards, and like objects. A flagrant piracy explosion over the past decade involving many of the foregoing products has plagued many industries. Alternatively, counterfeiting of such objects has become a thriving business and the need to identify authentic from counterfeit objects is of great importance.

Often, these objects have no serial number or other unique means of identification, or the number can be removed easily following a theft. Thus, a simple method for reliably identifying such objects would be welcomed by the owners. Especially welcome would be a do-it-yourself kit so that ordinary citizens (non-professionals) would be able to uniquely and permanently identify their valuable possessions. For present purposes, "valuable" is used in a relative sense in that the owner of the object values the object, whether for monetary, investment, or sentimental purposes.

In U.S. Pat. No. 5,599,578, there is disclosed a technique for labeling objects for their identification and/or authentication involving the use of a combination of a mark visible to the naked eye and a mark invisible to the naked eye. The invisible mark or component of the system is one or more of an ultraviolet radiation (UV) dye, an infrared (IR) dye, an ink that displays a selected measurable electrical resistivity, or a biologic marker which may be a protein, amino acid, DNA, polypeptide, hormone, or antibody.

U.S. Pat. No. 6,030,657 is directed to a method for labeling an object for its identification. This method includes providing a biologic marker labeled with an agent that emits selected detectable wavelengths of energy when exposed to infrared radiation (IR), and associating the labeled marker with the object, whereby, the object to be identified can be exposed to IR and emitted select wavelengths of energy from said agent detected. The agent can be an upconverting phosphor, a lanthenide ion (bound to a naphthalene group), or other chemical that emits selected detectable wavelengths of energy when exposed to infrared radiation (IR). The materials are encapsulated in an encapsulant that is resistant to the environment in which the materials are used such as, for example, an ink formulation. However, the encapsulant can be opened (e.g., by selective dissolving) and the materials inside (e.g., biologic, IR emitting, etc.) determined. A presently preferred encapsulant is casein which has been self cross-linked to provide resistance to hydrophobic ink formulations in which it desirably is placed.

A series of patents, U.S. Pat. Nos. 6,536,672, 6,354,501, and 6,203,069, propose combinations of IR phosphors and UV sensitizers for use along with bar codes to label products for identification and authentication. A spectrum analyzer therefor is disclosed in U.S. Pat. No. 6,274,873.

BROAD STATEMENT OF THE INVENTION

Kit for labeling an object for identification thereof includes an inkpad containing an ink bearing an ultra-violet (UV) radiation sensitive dye, a binder, a first biologic mark, and being invisible in the absence of UV light. The kit also includes an integral writing instrument housing a UV light and an ink pen bearing ink that bearings a UV dye and a second biologic marker. The kit further contains an ink pen housing an ink bearing a UV dye and a third biologic marker, and being invisible in the absence of UV light. An inventory list to record objects labeled with said kit is included in the kit additionally.

The method for labeling an object for identification thereof, which comprises the steps of placing a finger on the inkpad; placing the finger on a surface at a pre-determined location of an object to be labelled to create a fingerprint on the surface; creating a mark on the surface with the ink pen; and recording the object labeled, the fingerprint applied and its location, and the mark on the ledger.

For present purposes "fingerprint" and "finger" include any and all fingers of a person's hand, including the thumb of the person.

BRIEF DESCRIPTION OF THE DRAWINGS

For a fuller understanding of the nature and advantages of the present invention, reference should be had to the following detailed description taken in connection with the accompanying drawings, in which:

FIG. 3 is a perspective view of the foam block having cutouts for housing the components of the kit;

FIG. 4 is the inventory ledger component of the kit;

FIG. 5 is the inkpad component of the kit;

FIG. 6 shows the tamper proof tags component of the kit;

FIG. 7 is the wavelength generator component of the kit;

FIG. 8 is the security ink pen component of the kit.

DETAILED DESCRIPTION OF THE INVENTION

Once an object is identified and verified, it can be labeled in accordance with the inventive kit disclosed herein so that its identification at a later date is materially enhanced. Based upon the foregoing description, it can be appreciated that personal property owners, law enforcement personnel, and insurance companies all can use the assistance which can be provided for them in properly identifying and verifying the ownership of household goods and other personal property. The present invention provides such assistance by providing an "invisible" label, the location of which on the object is not published and is not apparent to the naked eye. Only upon the application of selected wavelengths of energy at the correct, pre-determined location on the object is the fingerprint label perceptible. When articles are lost or stolen, initial ownership can be established based on the fingerprint and other UV label located on the personal property. Analyzing for the biologic market included in the inks confirms the identification of the labeled personal property, for example, by matching DNA.

By properly preserving the secrecy of the fingerprint labeling location and its presence, the value of the fingerprint label is enhanced. That is, the location of the fingerprint label can be controlled, as well as whose fingerprint is applied thereto. In fact, combinations of fingerprints can be utilized at the same or at different locations on the object for providing further foolproof means for labeling the object. Since Dactyloscopy is a recognized science by the courts for identification, recognized experts for reading fingerprints can be utilized for verifying the authenticity of the fingerprint labels. As noted above, the fingerprint labeling technique of the present invention can be utilized on any object. Objects as commonplace as television sets, videocassette recorders, and the like can be identified by the fingerprint label technique of present invention. Should such objects be stolen, the criminal would not be able to mask the identity of the object by removing serial numbers applied by the manufacturer. Indeed, the fingerprint label could be located at almost any surface of the object so that its identity would be firmly established.

Figure 1:
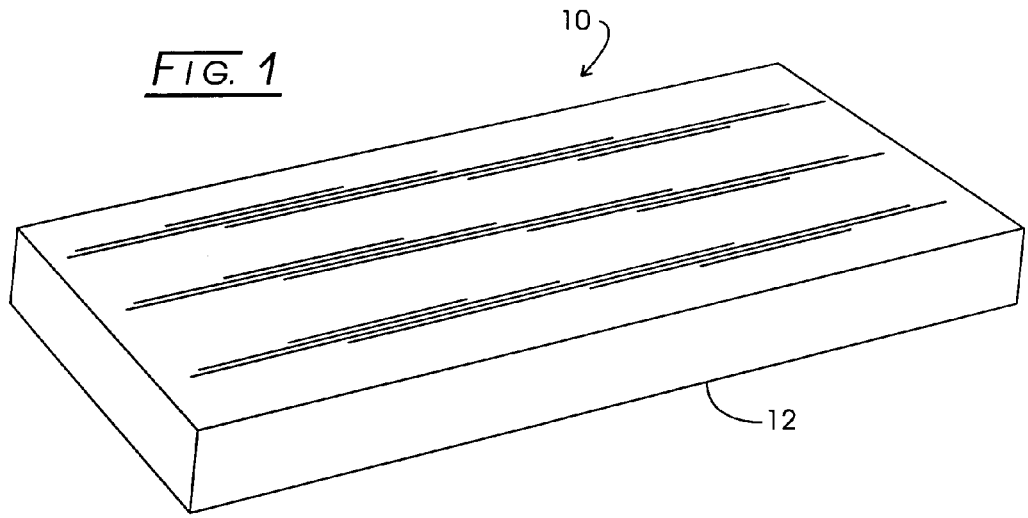
FIG. 1 is a perspective view of the kit of the personal invention.
Figure 2:
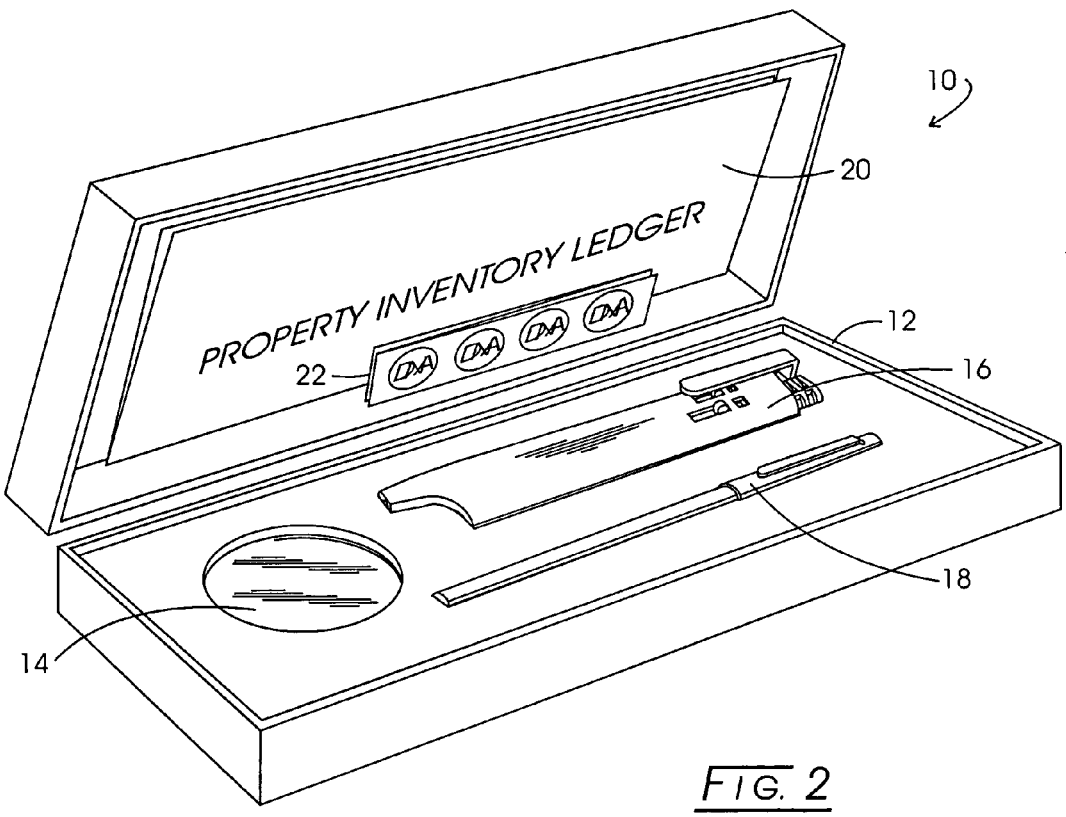
FIG. 2 is a perspective view of the kit of FIG. 1 opened to reveal the components of the kit.

Referring now to the drawings, FIG. 1 shows a kit, 10, wherein a cardboard box, 12, houses the kit components. Other materials of construction, e.g., plastic, could be used for box 12, which can have a detachable lid or hinged lid. Box 12 is opened in FIG. 2 to reveal the kit components, to wit: a security ink pad assembly, 14; a security integral writing/UV light instrument, 16; a security ink pen, 18; a property inventory ledger, 20; and tamper proof tags, 22. Instructions for use of kit 10 (not separately shown) also are included inside box 12 or printed directly on box 12, or printed on a label affixed to box 12. Property inventory ledger 20 also could contain the directions for use of kit 10. The exact placement of the instructions is immaterial and can be placed in a location as is necessary, desirable, or convenient to the manufacturer. FIG. 3 shows that a foam block, 24, contains cutouts for housing kit components for shipping, storage, and use of kit 10 without damage to the kit contents. Other materials of construction for block 24 can be used according to the desires of the manufacturer of kit 10.

FIG. 5 shows security inkpad assembly 14 to include a closable housing, 26, and a security inkpad, 28. Inkpad 14 can be made of suitable material, including, for example, porcelain, rubber, fabric, or like, which pad retains the security ink for repeated use. Housing 26 desirable is an air-tight closure made from plastic or other suitable material. The security ink is composed of a UV fluorescent dye, a binder, and a biologic marker, as further described below. Fluorescent dyes include, for example, various rhodamines, such as, for example, Columbia Blue, 8-hydroxy-1,3,6-pyrenetrisulfonic acid trisodium salt (HOPSA, Eastman Chemical Company), Rhodamine B, or Hostacell yellow 8G (American Hoechst Corporation).

Appropriate binders include, for example, hardenable materials, including, for example, thermoplastic resins. Thermoset resins, and penetrating carriers effective in establishing chemical and/or physical association of the UV dye with the surface of the object being labeled. Thermoplastic resins include, for example, polyesters, urethanes, acrylics, ethylene vinyl acetate copolymers, vinyl chloride homopolymers and copolymers, styrene butadiene polymers, styrene acrylonitrile polymers, silicone resins, cellulosic resins, ionomers, and the like and mixtures thereof. Thermosetting materials include, for example, air drying polyesters, urethane-forming resins formulated from polyols and polyisocyanates, conventional two-component epoxy resins with conventional hardeners (e.g., polyamine resins), UV curable resins, moisture-curable urethane resins, enzyme-curable resins, electron beam curable resins, radio-frequency curable resins, and the like, and mixtures thereof. So long as the binder, optionally with a solvent, can retain the UV dye, and provide permanence to the fingerprint on the object being labeled, such binder is suitable for use in accordance with the precepts of the present invention.

Specific thermoplastic and thermoset resins include, for example, latex copolymers including methyl methacrylate/ethyl acrylate copolymers, styrene/butyl acrylate copolymers, styrene/butadiene copolymers, styrene/butyl acrylate/methacrylic acid/acrylic acid copolymers, methyl methacrylate/methacrylic acid/ethyl acrylate copolymers, methacrylic acid/butadiene/styrene copolymers, methyl methacrylate/butyl acrylate copolymers, butadiene/methacrylic acid copolymers, butadiene/acrylonitrile/methacrylic acid copolymers, butadiene/acrylonitrile/methacrylic acid copolymers, methacrylic acid/methyl methacrylate/ethyl acrylate/acrylic acid/ethyl acrylate copolymers; tongue oil/fumaric acid/pentaerythritol copolymers, and the like and mixtures thereof. Thus, it will be observed that a wide variety of thermoplastic and thermoset materials are suitable for use in accordance with the precepts of the present invention.

Penetrating carriers may be used with some objects to be labeled. Such penetrating carriers, which are effective in establishing chemical and/or physical association of the UV dye with the surface of the object being labeled, may be termed as solvents, which optionally may be reactive, e.g., UV curable acrylic monomers. Alternatively, for some substrates, such as paper or plastic, a vegetable oil or other carrier may be effective in penetrating into the substrate and carry the UV dye along with it. Whether the vegetable oil or other solvent remains or evaporates does no matter so long as the UV dye in the form of the fingerprint remains firmly established or permanent for the requisite time appropriate for the object being labeled. Of course, the label also should not be readily perceptible to the human eye without the aid of UV radiation.

For present purposes, "permanent" as applied to the fingerprint label on the object means that the fingerprint is incapable of being removed from the object in the ordinary course of intended handling and usage of the object for a time adequate for identification and/or verification of the object to occur. For some objects, it may be desirable that the fingerprint label remains affixed to the object and identifiable in the presence of UV radiation for many years. Such objects would include works of art, household appliances, machinery, automobiles, automobile parts, and the like.

In a broader sense, the "label" applied to the object need only be a mark, which creates a permanent impression thereof, which is perceptible only in the presence of UV radiation. Since pad 28 bears both the binder and UV dye, any convenient stamp or similar imprinting implement can be utilized to apply a variety of forms of marks including a digitized code for fingerprints, a person's Social Security or drivers license number, a person's birthday, or any other series of numbers. For that matter, designs and logos can be applied as a mark for creating a permanent impression thereof, which is perceptible only in the presence of UV radiation. The invention will be described with particularity for utilizing fingerprints as the invisible mark applied for labeling an object, though such description is by way of illustration and not limitation of the present invention. Additionally, pad 28 has been suitably sized to permit a thumb to be applied thereto for applying a thumbprint to the personal property being labeled.

Referring now to FIG. 7, integral writing instrument/UV light source 16 is depicted. Integral writing implement 16 includes a housing in which is disposed an ink reservoir terminated with a writing nib. The ink housed contains an agent (ultraviolet (UV) sensitizer, infrared (IR) phosphor) wherein the ink is visible only in the presence of select wavelengths of energy. A generator for generating the select wavelengths of energy also is disposed within the housing and is oriented to illuminate the ink dispensed by the writing nib. The housing also contains a switch to selectively actuate the generator. Advantageously, the writing nib is retractable into said housing and extensible outside said housing. The user activates the generator with the switch and is enabled to view characters and graphics created by the user. Deactivation of the generator renders the written ink invisible to the naked eye. Additionally, the ink may contain a biologic marker, as further described below. Further description of integral writing instrument/UV light source 16 can be found in Applicant's U.S. Ser. No. 10/624,296, filed on Jul. 22, 2003.

The wavelength generator housed in integral instrument 16 can comprise more than one generator should UV and IR wavelengths be desired and/or required for detecting both UV and IR agents dispersed in the ink. Also, more than one UV and/or IR generator can be housed within the integral writing implement of the present invention, say, for example, to detect the presence of more than one UV and/or R agent dispersed in the ink.

Security ink pen 18 is illustrated in FIG. 8. It is conventional in construction being formed of a barrel, 30, and a cap, 32. The ink housed within ink pen 18 may be visible to the naked eye or visible only in the presence of UV light. The ink also contains a biologic marker, as further described below. Ink pen 18 may be used to autograph the object being labeled or create other alphanumeric characters and/or graphic images on a surface of the object to provide further identification/authentication of the object.

Inventory ledger 20 in FIG. 4 is used to record each object labeled with kit 10, including, inter alia, the location of the mark on the object and the type of mark created. The user can use inventory ledger 20 to report a theft and provide the authorities with the necessary information that they can use to identify the object when it is recovered.

Tamper proof tags 22 can be applied to a surface of the labeled object to provide notice or warning to would be thieves that the object is protected by kit 10 and the object is traceable back to the owner.

An additional technique for implementing the present invention involves the application the fingerprint label to an object as described herein. Next, a fluorescent light from integral writing instrument 16 would be shined upon the surface whereat the fingerprint is located and a record, e.g., a photograph, of such surface and fingerprint label taken. The photograph would document the exact placement location of the fingerprint label. The photograph could be maintained within inventory ledger 22. The likelihood of a fingerprint being placed in the same location is remote, so that the fingerprint labeling technique of the present invention is a near-foolproof technique for labeling objects for their identification and verification. It will be appreciated that when the UV light is turned off, the "invisible" mark again becomes invisible to the observer. The mark can be rendered visible numerous times without affecting it or its ability to remain invisible in the absence of the UV light.

Moreover, the present invention can be implemented to even a further degree of sophistication utilizing the new breed of "high tech" fingerprint computer equipment, which currently is being put into service by some law enforcement agencies. This aspect of the invention involves the maintenance of a duplicate copy of the fingerprint label applied to the object either on a card, which the owner of the object retains or company offering such fingerprint labeling service retains it. If the labeled object were stolen and recovered, or its authenticity questioned, the fingerprint could be identified. By cross-referencing the identified fingerprint, the object, e.g., a DVD player, actually could be identified and the true owner determined. This technique could be done through the use of a single fingerprint classification and identification system that currently exists within the law enforcement arena. Besides manual matching of fingerprints, the use of fingerprint computer equipment also could be implemented.

The ink in pad 28, integral writing instrument 16, and pen 18, also contains a genetic molecule, such as a DNA or other protein strand, for further verification. Biologic markers, such as amino acids and proteins are disclosed in U.S. Pat. No. 5,194,289. Such biologic materials can be profiled by gas chromatography which creates a standard for later comparison with a small (e.g., nanogram) sample of ink from a stolen object, a counterfeit object, or a diverted genuine object, which objects have been labeled in accordance with the precepts of the present invention. Additionally, U.S. Pat. No. 5,139,812 discloses the use of nucleic acid sequences in ink for identifying an object with a probe. U.S. Pat. No. 4,880,750 discloses the use of individual-specific antibodies (e.g., in an ink) for identification of security documents. U.S. Pat. No. 4,441,943 uses synthetic polypeptides for labeling explosives. British Patent No. 2,209,831 proposes to label objects with a nucleic acid, antibody, or antigen. U.S. Pat. No. 5,451,505 uses nucleic acids as taggants. U.S. Pat. No. 5,429,952 proposes to associate hapten with a product and then later detecting the presence of hapten with a complementary binding member and, thus, identify the product. MHC (major histocompatibility complex is yet another biologic marker suitable for use in the present invention. Thus, the term "biologic marker" should be construed broadly to include biologic materials (natural and synthetic, whole or fragments, naturally occurring, synthetic, and/or modified) for use in accordance with the precepts of the present invention. The disclosures of these citations are expressly incorporate herein by reference.

Such techniques also are not readily perceptible without the aid of special equipment and/or chemicals, which develop the presence of such markers. For present purposes, such markers are unique and not easily (if at all) replicated by the forger or counterfeiter. The foregoing biologic markers may be incorporated into a visible (of the same or a different color from the object or product being marked) or an invisible ink for use in labeling objects. It should be understood also that such biologic markers can be native or can be synthetic, including fragments, single chains, and a variety of additional forms currently developed or yet to be developed. It may even be feasible to radiolabel some biologic or other markers and determine their presence thereby. U.S. Pat. No. 6,030,657 provides more information on biologic markers.

While both up-converting and down-converting phosphors also can be added to the ink, particularly useful phosphors are rare earth oxysulfides that fluoresce blue, green, and red at wavelengths of around 475, 545, and 660 nm, respectively, such as selected from those phosphors as described in British patent application 2,258,659, published on Feb. 17, 1993, the disclosure of which is expressly incorporated herein by reference. Such phosphors are described as doped yttrium oxysulphide ($Y_2O_2S$), in which the dopants comprise, by weight of the oxysulphide, 4% to 50% of one or both of erbium (Er) and ytterbium (Yb). The material may comprise 1 to 50 ppm of one or more other lanthanide elements. Erbium and ytterbium may be replaced by thulium (Tm), holmium (Ho), or lutetium (Lu). The material may be in the form of particles whose average size is no more than 20 $\mu$m. Reference also is made to O'Yocom, et al., "Rare-Earth-Doped Oxysulfides for Gallium Arsenide-Pumped Lumines Devices", *Met. Trans.*, (1971), 2(3), 763–767, and Wittke, et al., "Erbium-Ytterbium Double Doped Yttrium Oxide. New Red-Emitting Infrared-Excited Phosphor", *J. Appl. Phys.*, (1972), 43(2), 595–600, the disclosures of which are expressly incorporated herein by reference.

With respect to the phosphors for IR detection, as described above (e.g., gallium oxysulfide), such up-converting phosphors require high (peak power) density photon radiation in order to excite emission. A 10 Hz pulsed LED in the 880 nm region of the spectrum with approximately 50 mW peak power should be suitable therefor. With respect to the detector equipment, a simple illuminator can be used where human perception of a greenish glow to determine the presence of the security phosphor is employed.

Another proposed illuminator/detector could be manufactured from a flashing LED with a very narrow pulse width due to the fact that human perception is unnecessary. Such detector could have an optical filter that blocks IR illumination frequency and passes only the frequency of radiation emitted by the phosphor, i.e., target frequency. Such a detector could be used under high ambient light conditions. Such a detector could be configured as a simple swipe-type reader or could have a hinged or removable gate to expose the phosphor to the LED.

A proposed illuminator/detector/reader could have the ability to read encoded patterns of the embedded phosphor, such as, for example, a bar code. The reading capability can be provided by suitable software, such as bar code reader engines.

As an alternative and/or adjunct to phosphors, luminescent labeling based on the lanthenide ions, samarium (III), europium (III), terbium (III), and dysprosium (III), bound by a chelating agent, could be used in the ink and/or attached to a component in the ink, including a DNA or other taggant. Exciting the naphthalene group attached to the chelating agent generates luminescence from such rare earth ions. Thus, light shined on the naphthalene group, which has a long-lived excited state, eventually gives up this excitation energy to the lanthenide ion, which responds by emitting light. Because of the way that the lanthenide ions are linked to naphthalene, a single wavelength of light can excite all four labels, each of them emitting light of a characteristic wavelength. Moreover, the emission bandwidths of the lanthenide ions are narrow, even at room temperature in fluid solution, allowing them to be detected simultaneously with minimum overlap.

Because the lifetimes of the excited states of these ions are relatively long, emission detection can be time-gated, virtually eliminating signals from background sources. Time-gating, for present purposes, comprehends use of a pulsed excitation source which allows a time delay between excitation and detection. Thus, the time delay before detection permits sources of interfering light, such as scattered excitation light, Raman scattering, and impurity fluorescence, to die down before detection is initiated. Another advantage of the lanthenide ions is that they are compatible with both capillary gel electrophoresis, which is considerably faster than conventional sequencing using slab gel electrophoresis, and computer collection and analysis of data. Additionally, measuring rise times, color ratios, etc., add additional advantage to use of the up-converting phosphors.

While the invention has been described with reference to presently known preferred embodiments, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In this application all units are in the metric system and all amounts and percentages are by weight, unless otherwise expressly indicated. Also, all citations referred herein are expressly incorporated herein by reference.

I claim:

1. Kit for labeling an object for identification thereof, which comprises:
   (a) an inkpad containing an ink bearing an ultra-violet (UV) radiation sensitive dye, a binder, a first biologic mark, and being invisible in the absence of UV light;
   (b) an integral writing instrument housing a UV light and an ink pen bearing ink that bears a UV dye and a second biologic marker;
   (c) an ink pen housing an ink bearing a UV dye and a third biologic marker, and being invisible in the absence of UV light; and
   (d) an inventory list to record objects labeled with said kit.

2. The kit of claim 1, which additionally comprises tamper proof tags.

3. The kit of claim 1, wherein said binder comprises a thermoplastic resin or thermoset resin.

4. The kit of claim 3, wherein said thermoplastic resin or thermoset resin is selected from the group consisting of a polyester, a polyurethane, an acrylic resin, an ethylene vinyl acetate copolymer, a vinyl chloride homopolymer or copolymer, a styrene butadiene polymer, a styrene acrylonitrile polymer, a silicone resin, a cellulosic resin, an ionomer, an air-drying polyester, an epoxy resin, and mixtures thereof.

5. The kit of claim 1, wherein said first biologic marker, said second biologic marker, and said third biologic marker are one or more the same biologic marker or different biologic markers.

6. The kit of claim 1, wherein said inkpad is adapted to receive the finger of a person for application of a fingerprint to an object to be labelled.

7. The kit of claim 1, which additionally contains instructions for its use.

8. The kit of claim 1, wherein one or more of said inks also contain an infrared upconverting phosphor.

9. A method for labeling an object for identification thereof, which comprises the steps of:
(a) accessing a kit, which comprises:
   (i) an inkpad containing an ink bearing an ultra-violet (UV) radiation sensitive dye, a binder, a first biologic mark, and being invisible in the absence of UV light;
   (ii) an integral writing instrument housing a UV light and an ink pen bearing ink that bears a UV dye and a second biologic marker;
   (iii) an ink pen housing an ink bearing a UV dye and a third biologic marker, and being invisible in the absence of UV light; and
   (iv) an inventory list to record objects labeled with said kit;
(b) placing a finger on said inkpad;
(c) placing said finger on a surface of an object to be labelled to create a fingerprint on said surface;
(d) creating a mark on said surface with said ink pen; and
(e) recording said fingerprint and said mark on said inventory list.

10. The method of claim 9, wherein said kit additionally comprises tamper proof tags, which are placed on said labelled object.

11. The method of claim 9, wherein said binder comprises a thermoplastic resin or thermoset resin.

12. The method of claim 11, wherein said thermoplastic resin or thermoset resin is one or more of a polyester, a polyurethane, an acrylic resin, an ethylene vinyl acetate copolymer, a vinyl chloride homopolymer or copolymer, a styrene butadiene polymer, a styrene acrylonitrile polymer, a silicone resin, a cellulosic resin, an ionomer, an air-drying polyester, or an epoxy resin.

13. The method of claim 9, wherein said first biologic marker, said second biologic marker, and said third biologic marker are one or more the same biologic marker or different biologic markers.

14. The method of claim 9, wherein said inkpad is adapted to receive the finger of a person for application of a fingerprint to an object to be labelled.

15. The method of claim 9, wherein said kit additionally contains instructions for its use.

16. The method of claim 9, wherein one or more of said inks also contain an infrared upconverting phosphor.

* * * * *